(12) United States Patent
Tamura et al.

(10) Patent No.: US 9,346,747 B2
(45) Date of Patent: May 24, 2016

(54) METHOD FOR STOPPING AMMOXIDATION REACTION

(71) Applicant: ASAHI KASEI CHEMICALS CORPORATION, Tokyo (JP)

(72) Inventors: Sho Tamura, Tokyo (JP); Sadao Shoji, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 14/430,714

(22) PCT Filed: Sep. 13, 2013

(86) PCT No.: PCT/JP2013/074893
§ 371 (c)(1),
(2) Date: Mar. 24, 2015

(87) PCT Pub. No.: WO2014/054408
PCT Pub. Date: Apr. 10, 2014

(65) Prior Publication Data
US 2015/0274648 A1    Oct. 1, 2015

(30) Foreign Application Priority Data

Oct. 1, 2012 (JP) ................................. 2012-219398

(51) Int. Cl.
*C07C 253/24*    (2006.01)

(52) U.S. Cl.
CPC .................................. *C07C 253/24* (2013.01)

(58) Field of Classification Search
CPC .................................................... C07C 253/24
USPC ................. 502/312, 248, 311, 305, 321, 211;
558/319, 323, 318, 303, 325, 308
See application file for complete search history.

(56) References Cited

U.S. PATENT DOCUMENTS

| | | | | |
|---|---|---|---|---|
| 3,501,517 A | * | 3/1970 | Hughes | B01J 8/1836 422/139 |
| 5,179,215 A | * | 1/1993 | Ramachandran | C07C 17/152 549/247 |
| 5,907,053 A | * | 5/1999 | Sakai | C07C 253/24 558/435 |
| 5,973,186 A | * | 10/1999 | Midorikawa | B01J 8/1827 558/319 |
| 6,033,632 A | * | 3/2000 | Schwartz | B01D 53/228 210/500.25 |
| 2004/0220434 A1 | * | 11/2004 | Brophy | B01J 19/0093 568/959 |
| 2006/0111575 A1 | | 5/2006 | DeCourcy et al. | |
| 2009/0299094 A1 | | 12/2009 | Fukuda et al. | |
| 2011/0218352 A1 | | 9/2011 | Besecker et al. | |
| 2011/0288324 A1 | | 11/2011 | Jacquot et al. | |
| 2011/0306788 A1 | | 12/2011 | Tanimoto et al. | |
| 2013/0289298 A1 | * | 10/2013 | Tateno | C07C 253/24 558/319 |
| 2014/0011896 A1 | | 1/2014 | Arai | |

FOREIGN PATENT DOCUMENTS

| | | |
|---|---|---|
| CN | 102176966 A | 9/2011 |
| JP | 11-209331 A | 8/1999 |
| JP | 11-263745 A | 9/1999 |
| JP | 2002-265431 A | 9/2002 |
| JP | 2006-143730 A | 6/2006 |
| JP | 2009-84167 A | 4/2009 |
| JP | WO 2010/103605 A1 | 9/2010 |
| JP | 2012-510971 A | 5/2012 |
| JP | 2012-207142 A | 10/2012 |
| WO | WO 2006/134852 A1 | 12/2006 |
| WO | WO 2012/096367 A1 | 7/2012 |

OTHER PUBLICATIONS

Ushikubo et al. "Ammoxidation of Propane over Catalysts Comprising Mixed Oxides of Mo and V" J. Catal. 1997, 169, 394-396.*
European Search Report issued Sep. 29, 2015, in European Patent Application No. 13843666.2.
International Search Report issued in PCT/JP2013/074893, mailed on Dec. 17, 2013.

* cited by examiner

*Primary Examiner* — Nyeemah A Grazier
*Assistant Examiner* — Amanda L Aguirre
(74) *Attorney, Agent, or Firm* — Birch, Stewart, Kolasch & Birch, LLP

(57) ABSTRACT

An object of the present invention is to provide a method for, when stopping an ammoxidation reaction of propane, stopping the ammoxidation reaction safely and quickly, without causing a deterioration in catalytic activity or acrylonitrile yield. The method for stopping an ammoxidation reaction includes a supply stopping step of stopping a supply of propane, an oxygen-containing gas, and ammonia to a reactor where an ammoxidation reaction of propane is being carried out using a catalyst, and a reaction stopping step of supplying an inert gas to the reactor in an amount 10 to 300 times the catalyst volume per hour until the catalyst temperature reaches 380° C. or less, wherein after the supply stopping step, a time required until the catalyst temperature decreases to 360° C. or less is within 10 hours.

2 Claims, No Drawings

METHOD FOR STOPPING AMMOXIDATION REACTION

TECHNICAL FIELD

The present invention relates to a method for stopping an ammoxidation reaction.

DESCRIPTION OF THE RELATED ART

Background Art

Conventionally, a method has been known for producing an unsaturated nitrile by an ammoxidation reaction, which is a kind of vapor-phase contact oxidation reaction, using an olefin such as propylene as a raw material. Recently, a method has been drawing attention for producing an acrylonitrile by using propane instead of propylene in an ammoxidation reaction. Industrial production of acrylonitrile is carried out at a high temperature exceeding 300° C. in a large reactor. Therefore, during regular inspections or during an emergency, it is desirable to stop the reaction quickly and safely. However, it is also necessary to pay attention so that the catalyst does not degrade when stopping the reaction. Therefore, methods for stopping ammoxidation reaction are being investigated in order to stop a hot, large reactor quickly and safely while preventing degradation of the catalyst.

In Patent Literature 1, it is disclosed that when producing by an ammoxidation reaction of propane or isobutane a corresponding unsaturated nitrile at a temperature of 380 to 500° C. in a fluidized bed reactor, the supply of a combustible gas and a gas containing molecular oxygen is continued while reducing the temperature to 300° C. even after the supply of the raw material gases for the ammoxidation reaction has been stopped. Patent Literature 1 discloses that it is preferred for the combustible gas included in the gas containing molecular oxygen that is supplied to the reactor to be in the range of 0.1 to 30% by volume.

In Patent Literature 2, it is disclosed that when stopping an ammoxidation reaction of propylene or isobutylene that uses a fluidized bed reactor, after the supply of an oxygen-containing gas, ammonia, and the propylene or isobutylene to the reactor has been stopped, an inert gas is supplied to the reactor in an amount 1 to 1,000 times that of the catalyst layer volume. Alternatively, it is disclosed that after the supply of propylene or isobutylene to the reactor has been stopped, the ammoxidation reaction is stopped by supplying an oxygen-containing gas to the reactor in an amount 0.5 to 5 times the catalyst layer volume, or by supplying an oxygen-containing gas and ammonia to the reactor in an amount 3 to 1,000 times the catalyst layer volume.

CITATION LIST

Patent Literature

Patent Literature 1: Japanese Patent Laid-Open No. 11-209331
Patent Literature 2: Japanese Patent Laid-Open No. 2002-265431

SUMMARY OF INVENTION

Technical Problem

However, according to investigations by the present inventors regarding methods for stopping an ammoxidation reaction of propane, when the inner diameter of the reactor is on a scale that exceeds several meters, a great deal of time is required to stop the supply of propane and ammonia in the stopping method described in Patent Literature 1, so that the reaction cannot be stopped quickly while preventing degradation of the catalyst. Further, in Patent Literature 2, although the total amount of the inert gas supplied to the reactor after stopping the supply of propylene is described, based on this method, a deterioration in activity due to degradation of the catalyst occurs, so that the acrylonitrile yield deteriorates.

Since the ammoxidation reaction of propane is a divergently exothermic reaction, temperature control is more difficult than in the ammoxidation reaction of propylene, so that heat removal from the reactor becomes very important. Consequently, a fluidized bed reactor is selected in which temperature control is comparatively easy and good. Further, since the catalyst particles used in a fluidized bed reaction are very small and in a vigorously mixed fluid state, there is also the advantage that an explosion does not occur even in the presence of a high concentration of a flammable gas, so that the reaction can be carried out comparatively safely. However, at locations where the amount of catalyst particle in the gas is sparse, such as at the upper section of the reactor and the outlet, a difficult-to-control combustion reaction can occur if the gas composition reaches the combustible range. In a normal operating state, a difficult-to-control combustion reaction is unlikely to occur because the reaction conditions are controlled while taking into account suppression of a combustion reaction in the reactor. However, during a reaction stopping operation, there is a period of very high risk due to the possibility of the gas composition reaching the combustible range at the upper section of the reactor or the reactor outlet although for a short time. From the perspective of placing importance on safety, a method is preferred in which first the supply of the oxygen-containing gas is stopped, and then the supply of propane and ammonia is successively stopped. However, if the catalyst is exposed to the propane or ammonia under a high temperature, catalyst degradation occurs due to a reductive action, and the catalyst performance irreversibly deteriorates.

Therefore, with the known methods, it is difficult to achieve both suppressed catalyst degradation and safe and quick reaction stopping in an ammoxidation reaction of propane.

The present invention has been made in view of the above-described problems, and it is an object of the present invention to provide a method for, when stopping an ammoxidation reaction of propane, stopping the ammoxidation reaction safely and quickly, without causing a deterioration in catalytic activity or acrylonitrile yield.

Solution to Problem

As a result of diligent research into resolving the above-described problems, the present inventors discovered that when stopping an ammoxidation reaction of propane, by supplying an inert gas to a reactor in an amount 10 to 300 times the catalyst volume per hour after stopping the supply of propane, an oxygen-containing gas, and ammonia to the reactor until the catalyst temperature reaches 380° C. or less, the ammoxidation reaction of propane can be stopped safely and quickly while preventing a deterioration in catalytic activity, thereby arriving at the present invention.

Namely, the present invention is as follows.

[1] A method for stopping an ammoxidation reaction comprising:

a supply stopping step of stopping a supply of propane, an oxygen-containing gas, and ammonia to a reactor where an ammoxidation reaction of propane is being carried out using a catalyst; and a reaction stopping step of supplying an inert gas to the reactor in an amount 10 to 300 times the catalyst volume per hour until a catalyst temperature reaches 380° C. or less, wherein after the supply stopping step, a time required until the catalyst temperature decreases to 360° C. or less is within 10 hours.

[2] The method for stopping an ammoxidation reaction according to the item [1], wherein the catalyst is a catalyst comprising Mo, V, Nb, and Sb.

[3] A method for producing an acrylonitrile comprising:

a supply stopping step of stopping a supply of propane, an oxygen-containing gas, and ammonia to a reactor where an ammoxidation reaction of propane is being carried out using a catalyst; and a reaction stopping step of supplying an inert gas to the reactor in an amount 10 to 300 times the catalyst volume per hour until a catalyst temperature reaches 380° C. or less, wherein after the supply stopping step, a time required until the catalyst temperature decreases to 360° C. or less is within 10 hours.

Advantageous Effects of Invention

According to the present invention, a method is realized for stopping an ammoxidation reaction that is capable of stopping the ammoxidation reaction safely and rapidly, while suppressing a deterioration in the catalytic activity and acrylonitrile yield.

DESCRIPTION OF EMBODIMENTS

A mode for carrying out the present invention (hereinafter referred to as "present embodiment") will now be described in more detail below. However, the present invention is not limited to the following embodiment. The present invention may be carried out while making various modifications within the scope of the invention.

[Method for Stopping an Ammoxidation Reaction]

The method for stopping an ammoxidation reaction according to the present embodiment includes:

a supply stopping step of stopping a supply of propane, an oxygen-containing gas, and ammonia to a reactor where an ammoxidation reaction of propane is being carried out using a catalyst; and a reaction stopping step of supplying an inert gas to the reactor in an amount 10 to 300 times the catalyst volume per hour until the catalyst temperature reaches 380° C. or less, wherein after the supply stopping step, a time required until the catalyst temperature decreases to 360° C. or less is within 10 hours. In the following, an ammoxidation reaction step will be described, followed by, a description of the method for stopping an ammoxidation reaction according to the present embodiment.

(Ammoxidation Reaction)

Acrylonitrile is produced by carrying out an ammoxidation reaction of propane by bringing propane, ammonia, and an oxygen-containing gas into contact with a catalyst in a reactor.

(Raw Materials: Propane, Ammonia, and Oxygen-Containing Gas)

The raw materials propane and ammonia are not limited to high-purity products. For example, industrial grade propane gas or ammonia gas can be used, such as propane that contains 5.0 vol % or less of impurities such as ethane, ethylene, n-butane, or isobutane, and ammonia containing 1.0 vol % or less of impurities such as water.

The oxygen-containing gas is not especially limited. Specific examples that can be used include air, oxygen-enriched air, pure oxygen, or a gas such as these diluted with an inert gas such as helium, argon, carbon dioxide, or nitrogen, or diluted with steam. Among these, when using on an industrial scale, it is preferred to use air due to its convenience.

(Catalyst)

The catalyst is not especially limited, as long as it can be used in an ammoxidation reaction of propane. Specifically, it is preferred that Mo, V, Nb, and Sb are contained. Although the reason is not clear, catalysts that contain Mo, V, Nb, and Sb as essential components tend to form a bronze structure that has good crystallinity, which is thought to help exhibit good catalytic ability during the ammoxidation reaction of propane.

From the perspectives of improving the selectivity of the target product and carrying out a long-term flow reaction, a more preferred composition that is included in the catalyst is represented by the following formula. $Mo_1V_aNb_bSb_cX_dZ_eO_n$ Wherein component X represents one or more elements selected from the group consisting of W, Te, Bi, and Mn, component Z represents one or more elements selected from the group consisting of La, Ce, Pr, Yb, Y, Sc, Sr, and Ba, and a, b, c, d, e, and n represent an atom ratio of each element per Mo atom, with a being $0.05 \leq a \leq 1$, b being $0.01 \leq b \leq 1$, c being $0.01 \leq c \leq 1$, d being $0 \leq d \leq 1$, e being $0 \leq e \leq 1$, and n being a number determined based on the atomic value of the constituent metal.

The atom ratio a of V per Mo atom is $0.05 \leq a \leq 1$, preferably $0.075 \leq a \leq 0.7$, and more preferably $0.1 \leq a \leq 0.4$. Setting the atom ratio a in this range tends to allow a more suitable propane activity to be obtained and to better suppress acrylonitrile degradation. The atom ratio b of Nb per Mo atom is $0.01 \leq b \leq 1$, preferably $0.02 \leq b \leq 0.7$, and more preferably $0.03 \leq b \leq 0.4$. Setting the atom ratio b in this range tends to allow a more suitable propane activity to be obtained and to better suppress acrylonitrile degradation. The atom ratio c of Sb per Mo atom is $0.01 \leq c \leq 1$, preferably $0.03 \leq c \leq 0.8$, and more preferably $0.05 \leq c \leq 0.5$. Setting the atom ratio c in this range tends to allow the ammoxidation reaction to proceed more easily. Further, a/c, which is the atom ratio between V and Sb, is preferably $0.5 \leq a/c \leq 2.0$, more preferably $0.6 \leq a/c \leq 1.8$, and even more preferably $0.7 \leq a/c \leq 1.6$. Setting so that a/c is in this range tends to better suppress degradation of the generated acrylonitrile.

The atom ratio d of X per Mo atom is $0 \leq d \leq 1$, preferably $0.001 \leq d \leq 0.5$, more preferably $0.003 \leq d \leq 0.4$, and even more preferably $0.005 \leq d \leq 0.3$. Setting the atom ratio d in this range tends to suppress acrylonitrile degradation activity much more, and to allow a more suitable propane activity to be obtained. From the perspective of long-term industrial usage, as component X, W, Bi, or Mn is preferred, and W is more preferred as it tends to suppress acrylonitrile degradation.

The atom ratio e of Z per Mo atom is $0 \leq e \leq 1$, preferably $0.0001 \leq e \leq 0.5$, and more preferably $0.0005 \leq e \leq 0.3$. Setting the atom ratio e in this range tends to suppress acrylonitrile degradation and ammonia combustion.

It is preferred that the carrier on which the above-described catalyst is supported has silica as a main component. When the catalyst is supported by a carrier that has silica as a main component, a high mechanical strength tends to be obtained. Consequently, such a catalyst can be preferably used in the below-described vapor-phase contact ammoxidation reaction that uses a fluidized bed reactor. When the carrier has silica as a main component, the silica content in the carrier is preferably, based on the total mass of the catalyst and the carrier, 20 to 70% by mass in terms of $SiO_2$, more preferably 25 to 65% by mass, and even more preferably 30 to 60% by mass. From the perspectives of strength and preventing powderization, the silica carrier content is preferably 20% by mass or more based on the total mass of the catalyst and the carrier. If the silica content is 20% by mass or more, also when the catalyst is used industrially, stable operation can be carried out, and loss of the supported catalyst tends to be low, which is preferable from an economic cost perspective, too. Further, from the perspectives of obtaining sufficient activity and properly setting the required amount of catalyst, it is preferred that the silica carrier content is preferably 70% by mass or less based on the total mass of the catalyst and the carrier. Especially in the case of a fluidized bed reaction, if the silica content is 70% by mass or less, the specific gravity of the catalyst is appropriate, so that it is easy to produce a good fluid state.

(Catalyst Production Method)

The method for producing the above-described catalyst is not especially limited. Specifically, a method that includes the following three steps may be employed.

Step (1): Step of obtaining a raw material blend solution by blending the raw materials Step (2): Step of obtaining a catalyst precursor by drying the raw material blend solution obtained in step (1)

Step (3): Step of obtaining a catalyst by calcining the catalyst precursor obtained in step (2)

Here, "blend" refers to dissolving or dispersing the raw materials of the catalyst constituent elements in a solvent. The solvent is not especially limited, but an aqueous solvent is preferred. Further, "raw material" refers to a compound that includes a constituent element of the catalyst. Although the raw materials are not especially limited, specific examples that can be used include the following compounds.

Although the Mo and V raw materials are not especially limited, ammonium heptamolybdate [$(NH_4)_6Mo_7O_{24} \cdot 4H_2O$] and ammonium metavanadate [$NH_4VO_3$] respectively, may be preferably used.

Although the Nb raw material is not especially limited, niobic acid, an inorganic niobate, and an organic niobate can be preferably used. Among these, niobic acid is preferred. Niobic acid is represented as $Nb_2O_5 \cdot nH_2O$, and is also referred to as niobium hydroxide or niobium oxide hydrate. Further, a Nb raw material solution in which a molar ratio of dicarboxylic acid/niobium is 1 to 4 may also be preferably used as the Nb raw material. The dicarboxylic acid in this case is not especially limited, although oxalic acid is preferred.

Although the Sb raw material is not especially limited, diantimony trioxide [$Sb_2O_3$] is preferred.

The component X raw material is not especially limited, as long as the raw material contains one or more elements selected from the group consisting of W, Te, Bi, and Mn. A compound containing these elements or formed by solubilizing the metal of these elements in an appropriate reagent can be used. As the compound containing these elements, an ammonium salt, a nitrate, a carboxylate, ammonium carboxylate, a peroxocarboxylate, ammonium peroxocarboxylate, a halogenated ammonium salt, a halide, acetyl acetate, and an alkoxide can usually be used. Among these, it is preferred to use a water-soluble raw material, such as a nitrate or a carboxylate.

The component Z raw material is not especially limited, as long as the raw material contains one or more elements selected from the group consisting of La, Ce, Pr, Yb, Y, Sc, Sr, and Ba. A compound containing these elements or formed by solubilizing the metal of these elements in an appropriate reagent can be used. As the compound containing these elements, a nitrate, a carboxylate, ammonium carboxylate, a peroxocarboxylate, ammonium peroxocarboxylate, a halogenated ammonium salt, a halide, acetyl acetate, and an alkoxide can usually be used. Among these, it is preferred to use a water-soluble raw material, such as a nitrate or a carboxylate.

The raw material for the silica contained in the carrier is not especially limited. A silica sol or silica powder can be used for a part or the whole amount of the silica raw material. The silica powder is preferably produced by a high-temperature method. Using a silica powder that has already been dispersed in water facilitates the addition and mixture of the silica powder into a slurry. The dispersing method is not particularly limited. The silica powder can be dispersed by using a general homogenizer, homomixer, supersonic vibrator, or the like either singly or in combination.

(Reaction Conditions: Reaction Temperature)

Although the reaction temperature of the ammoxidation reaction is not especially limited, it is preferably 380 to 500° C., more preferably 390 to 490° C., and even more preferably 400 to 480° C. Setting the reaction temperature at 380° C. or more tends to enable the ammoxidation reaction of propane to proceed at a practical rate. Further, setting the reaction temperature at 500° C. or less tends to allow acrylonitrile degradation to be suppressed.

(Reaction Conditions: Pressure)

Although the reaction pressure of the ammoxidation reaction is not especially limited, a lower pressure tends to increase acrylonitrile selectivity. Therefore, the reaction pressure is preferably $0.2 \times 10^5$ to $5 \times 10^5$ Pa, more preferably $0.3 \times 10^5$ to $3 \times 10^5$ Pa, and even more preferably $0.4 \times 10^5$ to $1 \times 10^5$ Pa.

(Reaction Conditions: Raw Material Ratio)

The reaction method may be a recycling type method, in which the unreacted raw material gases are recovered and fed back to the reactor, or may be a single-flow method, in which the unreacted raw material gases are not recovered. However, the preferred composition ratio of the raw material gasses depends on the reaction method. For example, when carrying out the reaction by a single-flow method, since it is important to increase the propane conversion rate, it is preferred that the oxygen/propane molar ratio is comparatively high. The oxygen/propane molar ratio when carrying out the reaction by a single-flow method is preferably 0.5 to 4.5, more preferably 1.0 to 4.0, and even more preferably 1.5 to 3.5. On the other hand, when carrying out the reaction by a recycling type method, to increase acrylonitrile selectivity, it is preferred to set the oxygen/propane molar ratio comparatively low to suppress the propane conversion rate to a low level. The oxygen/propane molar ratio when carrying out the reaction by a recycling type method is preferably 0.2 to 3.5, more preferably 0.6 to 3, and even more preferably 1.0 to 2.5. However, since the composition ratio of the raw material gases may influence the outlet oxygen concentration, in either of these reaction methods, it is preferred to determine the composition ratio in consideration of achieving the desired range for the outlet oxygen concentration as well.

(Outlet Oxygen Concentration)

Although the outlet oxygen concentration of the reactor is not especially limited, it is preferred to adjust so that the outlet oxygen concentration is in the range of 0.1 to 6.0%, more preferably in the range of 0.3 to 5.5%, and even more preferably in the range of 0.5 to 5.0%. If the outlet oxygen concentration is in the above range, the redox rate of the catalyst can be maintained at a fixed level, degradation of the catalyst can be suppressed, and acrylonitrile can be produced more stably. Although the outlet oxygen concentration of the reactor can be adjusted by changing conditions such as the composition ratio of the raw material gases, the total flow rate of the raw material gases, the reaction temperature, the reaction pressure, the amount of catalyst, and the like, it is preferred to adjust the outlet oxygen concentration by the composition ratio of the raw material gases because this is easy to operate.

[Method for Stopping the Ammoxidation Reaction]
[Supply Stopping Step]

The supply stopping step according to the present embodiment is a step of stopping the supply of the propane, the oxygen-containing gas, and the ammonia to the reactor where the ammoxidation reaction of propane is carried out using a catalyst. It is preferred to, although not especially limited, stop the supply of the propane, the oxygen-containing gas, and the ammonia to the reactor simultaneously. By stopping simultaneously, catalyst degradation caused by the catalyst being exposed to propane and ammonia under high temperatures tends to be suppressed more. Here, "simultaneously" should not be strictly literally understood, it means that the supply of the propane, the oxygen-containing gas, and the ammonia is not stopped successively. Based on the method for stopping an ammoxidation reaction according to the present embodiment, the reaction can be safely stopped even if the supply of the propane, the oxygen-containing gas, and the ammonia is simultaneously stopped. Further, the reaction can be stopped comparatively quickly.

(Temperature at which the Supply of the Raw Materials is Stopped)

The temperature at which the supply of the raw materials is stopped is not especially limited. However, from the perspective of catalyst protection, it is preferred to carry out before departing from the suitable reaction temperature range for ammoxidation. It is preferred to start when the catalyst temperature is in the range of 380 to 500° C., more preferably in the range of 390 to 490° C., and even more preferably in the range of 400 to 480° C. Starting to stop when the catalyst temperature is 500° C. or less tends to suppress inclusion of excess oxygen in the catalyst, and tends to make it more difficult for oxidative degradation to occur. Further, starting to stop when the catalyst temperature is 380° C. or more tends to make it more difficult for reductive degradation of the catalyst caused by a stagnating in the supply of oxygen to the catalyst to occur.

[Reaction Stopping Step]

The reaction stopping step according to the present embodiment is a step in which the ammoxidation reaction of propane is stopped by supplying an inert gas to the reactor in an amount 10 to 300 times the catalyst volume per hour until the catalyst temperature reaches 380° C. or less. To stop the reaction while suppressing catalyst degradation and ensuring the safety of the reactor, after the supply stopping step, an inert gas is supplied in an amount 10 to 300 times, preferably 10 to 250 times, and more preferably 10 to 200 times the catalyst volume per hour. By setting the amount of inert gas supplied within this range, the ammoxidation reaction can be stopped safely and quickly while suppressing a deterioration in the catalytic activity and in the acrylonitrile yield much more. If the amount of inert gas supplied per hour is less than 10 times the catalyst volume, the gases generated when stopping the supply of the propane, oxygen-containing gas, and ammonia cannot be driven out. Consequently, the generated gases remain in the catalyst layer, and the catalyst degrades. Further, if the amount of inert gas supplied per hour is more than 300 times the catalyst volume, since a large amount of gas is flowing under ordinary pressure, the catalyst is blown away and scattered from the reactor in a large quantity. Consequently, such catalyst scattering cause safety problems and a large amount of catalyst to be lost.

Further, the inert gas supplied to the reactor is not especially limited. Specific examples include nitrogen, helium, and carbon dioxide. It is preferred that impurities such as water and oxygen in the inert gas are not more than 3.0% by volume, more preferably not more than 2.0% by volume, and even more preferably not more than 1.0% by volume. If the content of impurities is in this range, degradation of the catalyst due to the catalyst coming into contact with a high concentration of oxygen under a high temperature can be prevented.

(Catalyst Volume)

An example of the method for determining the catalyst volume includes calculating using bulk specific gravity. In the present embodiment, it is important to purge the raw material gases and generated gases that are present in gaps in the catalyst and are in contact with the catalyst when the reaction is stopped. Therefore, the catalyst volume is determined from bulk specific gravity, which includes the gaps. A specific example of a calculation method is to divide the weight of the catalyst loaded into the reactor by the bulk specific gravity. For example, if the amount of catalyst loaded into the reactor is 1,000 kg and the bulk specific gravity is 0.8 kg/L, the catalyst volume is 1.25 Nm$^3$. Although the method for measuring the bulk specific gravity is not especially limited, from the viewpoints of a catalyst having good fluidity used in a fluidized bed, and good reproducibility during measurement, it is preferred to employ a funnel loading method.

(Supply Until the Catalyst Temperature is 380° C. or Less)

The inert gas is supplied until the catalyst temperature is 380° C. or less. When the catalyst temperature reaches 380° C. or less, the supply of the inert gas may then be stopped, and an oxygen-containing gas such as air may be supplied instead. However, from the perspective of suppressing catalyst degradation, it is preferred to continue the supply of the inert gas until the catalyst temperature is 360° C. or less, and more preferably 340° C. or less. Setting so that the catalyst temperature is 380° C. or less makes it more difficult for catalyst degradation to occur even if the catalyst comes into contact with the raw material gases and generated gases. At 340° C. or less, there is almost no degradation of the catalyst. From the perspective of completely suppressing catalyst degradation, the supply of the inert gas may even be continued until the catalyst temperature is 200° C. or less.

(Method for Measuring the Catalyst Temperature)

Although the method for measuring the catalyst temperature is not especially limited, it is preferred to measure the temperature by placing in the catalyst layer a nozzle having a tip that is not open, inserting a thermometer into the nozzle, and measuring the temperature. Although the reaction temperature is basically almost the same everywhere in the catalyst layer, if the amount of catalyst is large, a slight temperature difference can occur in the catalyst layer. Therefore, it is preferred to place the nozzle at a plurality of locations, and take the average temperature thereof as the catalyst temperature.

When stopping the supply of the inert gas when the catalyst temperature reaches 380° C. or less, it is preferred to reduce the catalyst temperature even more rapidly by switching the inert gas to air, an oxygen-containing gas, and the like. In this case, to shorten the time, heat removal with a heat-removing pipe can also be carried out. For example, by also employing a heat-removing pipe in addition to the inert gas, the time required until the catalyst temperature decreases to 340° C. can be within 4 hours. The operation method of the heat-removing pipe is not especially limited. The temperature may be regulated by a known method while monitoring the temperature.

The time required until the catalyst temperature decreases to 360° C. or less after the supply stopping step is within 10 hours, preferably within 9 hours, and more preferably within 8 hours. If the time required until the catalyst temperature decreases to 360° C. or less is within the above range, the ammoxidation reaction can be stopped safely and rapidly while suppressing a deterioration in the catalytic activity and in the acrylonitrile yield much more.

(Change in the Catalyst Reduction Rate)

To exhibit a catalyst's inherent performance, it is important to maintain a suitable redox state. If the catalyst is reduced too much, reductive degradation occurs, which can lead to a deterioration in yield. Further, if the catalyst is oxidized too much, irreversible degradation can occur. Consequently, it is desirable for the reaction to stop at a point where the rate of change in the reduction rate of the catalyst before and after the reaction is stopped is at a low level. It is preferred that when the reduction rate of the catalyst before the reaction is stopped and the reduction rate of the catalyst after the reaction is stopped are compared, this rate of change is within 5%, more preferably within 4%, and even more preferably within 3%. If the rate of change is within this range, catalytic activity tends to be maintained better.

The "catalyst before the reaction is stopped" mentioned here refers to the catalyst before the supply stopping step that has been extracted from the reactor uniformly and without change in the catalyst state while still being used in the ammoxidation reaction. Since the reaction is basically carried out without changing the reduction rate during the reaction, a catalyst extracted from 1 minute to one month before the reaction is stopped can be considered as a catalyst before the reaction is stopped.

Further, the "catalyst after the reaction is stopped" mentioned here refers to a catalyst after the supply stopping step that has been extracted from the reactor after the supply of the propane, ammonia, and oxygen-containing gas is stopped.

(Method for Measuring Catalyst Reduction Rate)

The reduction rate of the catalyst can be determined by measuring the absorbance of the catalyst based on the absorption spectrum. Especially when using a catalyst that includes Mo and V in the ammoxidation reaction of propane, the redox state of the catalyst can be simply and accurately determined based on the absorbance of the catalyst measured using a visible-ultraviolet spectrophotometer.

Specifically, it is preferred to determine a normalized UV value using the following equation (1) based on the absorbance at 400 nm, 580 nm, and 700 nm of the absorption spectrum obtained by a diffuse reflection method using a visible-ultraviolet spectrophotometer. The normalized UV value acts as an index of the catalyst redox state, since a larger value indicates that the catalyst has been reduced, while a smaller value indicates that the catalyst has been oxidized.

$$\text{Normalized UV} = \{(580 \text{ nm absorbance}) - (400 \text{ nm absorbance})\} / \{(700 \text{ nm absorbance}) - (400 \text{ nm absorbance})\} \quad \text{Equation (1)}$$

(Catalyst Extraction Method)

The method for extracting the catalyst is not especially limited, as long as the catalyst in the reactor can be uniformly extracted. Examples include, in the case of a fluidized bed reaction, (1) a method of connecting a vessel to a nozzle protruding from the reactor, and (a) moving the catalyst in the reactor to the vessel by making the pressure in the vessel lower than that in the reactor and utilizing the difference in pressure, or (b) introducing from outside the reactor a gas for catalyst extraction to form a flow of gas from the reactor into the vessel that conveys the catalyst into the vessel, and (2) a method of attaching a vessel to a lower portion of the reactor and utilizing gravity to extract the catalyst.

If the pressure in the reactor is equal to or greater than atmospheric pressure, the above-described method (a) of utilizing a pressure difference is preferred due to its simplicity. The method for making the pressure in the vessel lower than that in the reactor may be a common method. If the pressure in the reactor is sufficiently higher than atmospheric pressure, the vessel may be maintained at atmospheric pressure, or a reduced pressure may be created in the vessel by making gas flow out using an ejector method.

In either of these methods, so that the physical properties of the extracted catalyst do not change, it is preferred that places in contact with the catalyst, such as the vessel interior and the insides of the connected pipes, are sufficiently purged in advance with an inert gas, such as nitrogen. Further, so that impurities or catalyst extracted in the past do not become mixed in the catalyst to be extracted, it is preferred to purge and clean the vessel interior and the insides of the pipes in advance with a suitable gas, an inert gas, and the like.

The location for extracting the catalyst may be a single location or a plurality of locations. Although the extraction location is not especially limited as long as the catalyst in the reactor can be uniformly extracted, for a fluidized bed, it is preferred to extract from a location where the flow state of the catalyst in the reactor is good and the catalyst density is thick, as it is believed that representative physical properties of the catalyst in the reactor can be obtained, and the catalyst can be extracted efficiently in a short time. In the reactor, a raw material gas distribution and a temperature distribution exist, so that the location can affect how the catalyst changes. In such a case, the catalyst can be extracted from a location thought to have average conditions, or the catalyst may be extracted from a plurality of locations based on the distribution. Further, a cyclone, pipes, shelves, and the like are arranged in the reactor. If there are locations where the catalyst flow state is thought to be different, in addition to extracting the catalyst from a location where the catalyst is flowing averagely and the flow state is good, the catalyst can also be extracted from a specific location.

Regarding the storage of the extracted catalyst, if the catalyst comes into contact at high temperatures with an oxidizing agent, such as oxygen, or a reducing agent, such as ammonia, the reduction rate of the catalyst changes. Therefore, if the catalyst temperature is high, such as immediately after extraction from the reactor, the catalyst is stored in an inert gas. If the catalyst is at an ordinary temperature, the catalyst can be stored in air without any problems.

(Reactor)

Although the reactor used in the above-described ammoxidation reaction is not especially limited, specifically, it is preferred to use a fluidized bed reactor. Catalyst obtained as described above is loaded into the fluidized bed reactor, and upper nozzles for supplying a gas containing propane and ammonia are placed pointing vertically downwards at a predetermined position above the bottom face of the catalyst loaded portion of the reactor. The placement positions may be set as the center of the reactor, and at the apexes of a square with the center of the reactor as its center (total of 5 locations). Separately from this, lower nozzles for supplying a gas containing oxygen are placed pointing vertically upwards at the bottom face of the catalyst loaded portion of the reactor. The placement positions of these lower nozzles may be set so as to overlap in the vertical direction the upper nozzles for supplying a gas containing propane and ammonia (total of 5 locations). For heat removal in the reactor, a stationary-used cooling coil and a cooling coil for fine adjustments to the temperature are placed in the catalyst dense layer.

The temperature and pressure in the reactor are set at the above-described reaction temperature and reaction pressure. Propane and ammonia from the upper nozzles and air from the lower nozzles are supplied in the above-described raw material ratio for a predetermined contact time. Consequently, acrylonitrile can be produced.

Further, to stop the ammoxidation reaction, specifically, the supply of the propane, ammonia, and air is concurrently stopped, and a predetermined amount of nitrogen per hour can be supplied from the lower nozzles that are placed pointing vertically upwards from the bottom face of the catalyst loaded portion of the reactor. The supply of the raw material gases is stopped. The catalyst layer temperature decreases to a predetermined temperature. Subsequently, the same amount of air as the nitrogen can be supplied until the temperature of the catalyst layer reaches 100° C. After thus stopping the ammoxidation reaction, the ammoxidation reaction can be restarted under the same conditions as before stopping the reaction using the catalyst remaining in the reactor.

[Acrylonitrile Production Method]

The method for producing an acrylonitrile according to the present embodiment includes a supply stopping step of stopping the supply of propane, oxygen-containing gas, and ammonia to the reactor where an ammoxidation reaction of propane is being carried out using a catalyst, and a reaction stopping step of supplying an inert gas to the reactor in an amount 10 to 300 times the catalyst volume per hour until the catalyst temperature reaches 380° C. or less. After the supply stopping step, the time required until the catalyst temperature reaches 360° C. or less is within 10 hours. Namely, the method for producing an acrylonitrile according to the present embodiment is a method that utilizes the above-described ammoxidation reaction stopping method. Consequently, the acrylonitrile yield can be maintained when the reactor is restarted without causing a deterioration in catalytic activity. Since the ammoxidation reaction can be stopped safely and quickly, this acrylonitrile production method is a low cost and highly efficient method.

EXAMPLES

The present invention will now be described in more detail based on the following Working Examples, Comparative Examples and Reference Examples. However, the present embodiment is not limited to these Working Examples.

[Acrylonitrile Yield]

In the Working Examples, Comparative Examples and Reference Examples, the acrylonitrile yield is based on the following definition. The number of moles of generated acrylonitrile was measured by analyzing in advance an acrylonitrile gas having a known concentration based on gas chromatography (GC) to obtain a calibration curve, and injecting a fixed amount of the gas generated by the ammoxidation reaction into GC.

Acrylonitrile yield(%)=(number of moles of generated acrylonitrile)/(number of moles of supplied propane)×100

[Rate of Change in the Reduction Rate of the Catalyst]

The reduction rate of the catalyst was measured as follows. The rate of change in the catalyst reduction rate was determined using the following equations (1) and (2) based on the absorbance at 400 nm, 580 nm, and 700 nm of the absorption spectrum obtained by setting the extracted catalyst in a sample holder and measuring based on a diffuse reflection method using an ultraviolet-visible spectrophotometer (V-660, manufactured by Jasco Corporation).

Normalized UV={(580 nm absorbance)−(400 nm absorbance)}/{(700 nm absorbance)−(400 nm absorbance)}      Equation(1)

Rate of change in the catalyst reduction rate=|((Normalized UV of catalyst before reaction stopping)−(normalized UV of catalyst after reaction stopping))|/(normalized UV of catalyst before reaction stopping)×100      Equation(2)

[Activity]

The activity was determined based on the following equation from the propane conversion rate and the contact time.

Activity=3.6×ln(100/(100−propane conversion rate))×contact time

[Propane Conversion Rate]

The propane conversion rate is based on the following definition. The number of moles of generated propane was measured by analyzing in advance a propane gas having a known concentration based on gas chromatography (GC) to obtain a calibration curve, and injecting a fixed amount of the gas generated by the ammoxidation reaction into GC.

Propane conversion rate(%)=(number of moles of reacted propane)/(number of moles of supplied propane)×100

[Contact Time]

The contact time is based on the following definition. The contact time is determined by dividing the catalyst volume by the corrected amount of raw material gas based on the reaction temperature and reaction pressure.

Contact time(sec)=catalyst volume(L)/amount of raw material gas(L/min)×273/(273+reaction temperature)×(1.013+reaction pressure)/1.013×60

[Method for Measuring Catalyst Temperature]

The temperature was measured by placing in the catalyst layer a nozzle having a tip that is not open and inserting a thermometer therein.

Working Example 1

Catalyst Preparation (Preparation of Niobium Mixed Solution)

A niobium mixed solution was prepared based on the following method. 1.530 kg of niobic acid [$Nb_2O_5$] containing 79.8% by mass and 2.894 kg of oxalic acid dihydrate [$H_2C_2O_4 \cdot 2H_2O$] were mixed in 10 kg of water. The charged molar ratio of the oxalic acid/niobium was 5.0, and the charged niobium concentration was 0.50 (mol-Nb/kg-solution). The solution was heated and stirred for 2 hours at 95° C. to obtain a mixed solution in which niobium was dissolved. This mixed solution was left to stand, ice-cooled, and then solids were separated by suction filtration to obtain a homogeneous niobium mixed solution.

(Oxalic Acid/Niobium Molar Ratio)

10 g of this niobium mixed solution was precisely weighed into a crucible, dried overnight at 95° C., and then heat treated for 1 hour at 600° C. to obtain 0.7895 g of $Nb_2O_5$. Based on this result, the niobium concentration was 0.594 (mol-Nb/kg-solution). 3 g of this niobium mixed solution was precisely weighed into a 300 mL glass beaker, charged with 200 mL of hot water of about 80° C., and then charged with 10 mL of 1:1 sulfuric acid. The obtained mixed solution was, under stirring while maintaining the solution temperature at 70° C. on a hot stirrer, titrated using ¼ N KMnO₄. The endpoint was taken as the point at which a faint pale peach color from the KMnO₄ continued for about 30 seconds or more. Based on a calculation using the following equation from the titration value, the oxalic acid concentration was 1.592 (mol-oxalic acid/kg-solution). Based on these results, the molar ratio of oxalic acid/niobium in this niobium mixed solution was calculated as being 2.68. The obtained niobium mixed solution was used as the niobium raw material solution (B₀) in the below-described catalyst preparation.

$$2KMnO_4+3H_2SO_4+5H_2C_2O_4 \rightarrow K_2SO_4+2MnSO_4+10CO_2+8H_2O$$

(Catalyst Preparation)

A catalyst having a charged composition formula represented by $Mo_1V_{0.20}Nb_{0.10}Sb_{0.20}W_{0.05}O_n/50.0$ wt %-SiO₂ was prepared as follows. 32.8 kg of ammonium heptamolybdate [$(NH_4)_6Mo_7O_{24} \cdot 4H_2O$], 4.31 kg of ammonium metavanadate [$NH_4VO_3$], and 5.40 kg of diantimony trioxide [$Sb_2O_3$] were charged into 88 kg of water, and the resultant mixture was heated for 1 hour at 95° C. under stirring to obtain an aqueous raw-material solution (I).

31.03 kg of the niobium mixed solution (B₀) was charged with 4.18 kg of hydrogen peroxide water containing 30 wt % of $H_2O_2$, and the resultant mixture was stirred and mixed for 10 minutes at room temperature to prepare an aqueous raw-material solution (II).

The obtained aqueous raw-material solution (I) was cooled to 70° C., charged with 58.86 kg of silica sol containing 34.0 wt % of SiO₂, then further charged with 6.27 kg of hydrogen peroxide water containing 30 wt % of $H_2O_2$, and the stirring was continued for another 30 minutes at 55° C. Next, the resultant mixture was sequentially charged with the aqueous raw-material solution (II), 64.26 g of an aqueous ammonium tungstate solution containing 50 wt % of WO₃, and a dispersion in which 20 kg of silica powder was dispersed in 270 kg of water, to obtain an aqueous mixed solution (III). The aqueous mixed solution (III) was aged at 50° C. for 2 hours 30 minutes from the addition of the aqueous raw-material solution (II) to obtain a slurry.

The obtained slurry was dried by feeding it into a centrifugal spray drier to obtain a dry powder having a microspherical shape. The inlet air temperature of the drier was 210° C., and the outlet air temperature was 120° C. This process was repeated several times. The obtained dry powder was loaded into a cylindrical calcining tube made of SUS having an inner diameter of 500 mm, a length of 3,500 mm, and a thickness of 20 mm. While rotating the tube under a nitrogen gas flow of 600 NL/min, the powder was calcined for 2 hours at 680° C. to obtain a catalyst.

[Vapor-Phase Contact Ammoxidation Reaction]

572 kg of the obtained catalyst was loaded into a SUS fluidized bed reactor having an inner diameter of 600 mm. The bulk specific gravity of the catalyst was 1 kg/L, and the catalyst volume was 572 L. Upper nozzles for supplying a gas containing propane and ammonia were placed pointing vertically downwards at a position 30 cm above the bottom face of the catalyst loaded portion of the reactor. The placement positions were the center of the reactor, and at the apexes of a square having 340 mm sides with the center of the reactor as its center (total of 5 locations). Lower nozzles for supplying a gas containing oxygen were placed pointing vertically upwards at the bottom face of the catalyst loaded portion of the reactor. The placement positions of the lower nozzles were set so as to overlap in the vertical direction the upper nozzles for supplying a gas containing propane and ammonia (total of 5 locations). For heat removal in the reactor, four stationary-used cooling coils and two cooling coils for fine adjustments to the temperature were placed in the catalyst dense layer.

At a reactor temperature of 440° C. and reaction pressure of 50 kPa, propane and ammonia were supplied from the upper nozzles and air was supplied from the lower nozzles at a propane:ammonia:oxygen molar ratio of 1:0.93:2.81 for a contact time of 2.91 sec·g/cm³. The oxygen concentration in the generated gas at the reactor outlet was 2.1%. This reaction was continued for 1 week.

[Ammoxidation Reaction Stopping]

The supply of propane, ammonia, and air was concurrently stopped, and 14,300 L of nitrogen (an amount 25 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 7 hours, and the time required until the temperature decreased to 360° C. was 8 hours. The supply of nitrogen was continued for 9 hours until the catalyst layer temperature reached 340° C. (inert gas cutoff temperature). Subsequently, the same amount of air as the nitrogen was supplied until the temperature of the catalyst layer reached 100° C. After the stopping of the ammoxidation reaction, the ammoxidation reaction was restarted under the same conditions as before the reaction was stopped using the catalyst remaining in the reactor (in Table 1, indicated as "After Re-SU" (hereinafter the same applies)). The acrylonitrile yield, the rate of change in the reduction rate of the catalyst before and after the reaction was stopped, and the activity are shown in Table 1. The inert gas flow time refers to the time from when the supply of the propane, ammonia, and air was stopped until the inert gas cutoff temperature was reached (hereinafter the same applies).

Working Example 2

Vapor-Phase Contact Ammoxidation Reaction

A vapor-phase contact ammoxidation reaction was carried out using the same catalyst as in Working Example 1. The reactor type, the reaction temperature, and the reaction pressure were the same as in Working Example 1. The supply of the raw material gases was carried out by supplying propane and ammonia from the upper nozzles and air from the lower nozzles at a propane:ammonia:oxygen molar ratio of 1:0.95:3 for a contact time of 3.05 sec·g/cm³. The oxygen concentration in the generated gas at the reactor outlet was 3.4%. This reaction was continued for 1 week.

(Ammoxidation Reaction Stopping)

The supply of propane, ammonia, and air was concurrently stopped, and 45,760 L of nitrogen (an amount 80 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 30 minutes.

The supply of nitrogen was continued for 5 hours 42 minutes until the catalyst layer temperature reached 375° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Working Example 3

Vapor-Phase Contact Ammoxidation Reaction

A vapor-phase contact ammoxidation reaction was carried out using the same catalyst as in Working Example 1. The reactor type, the reaction temperature, and the reaction pressure were the same as in Working Example 1. The supply of the raw material gases was carried out by supplying propane and ammonia from the upper nozzles and air from the lower nozzles at a propane:ammonia:oxygen molar ratio of 1:1:3.2 for a contact time of 3.15 sec·g/cm$^3$. The oxygen concentration in the generated gas at the reactor outlet was 3.5%. This reaction was continued for 1 week.
(Ammoxidation Reaction Stopping)

The supply of propane, ammonia, and air was concurrently stopped, and 85,800 L of nitrogen (an amount 150 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 4 hours, and the time required until the temperature decreased to 360° C. was 5 hours 12 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Working Example 4

Vapor-Phase Contact Ammoxidation Reaction

A vapor-phase contact ammoxidation reaction was carried out using the same catalyst as in Working Example 1. The reactor type, the reaction temperature, and the reaction pressure were the same as in Working Example 1. The supply of the raw material gases was carried out by supplying propane and ammonia from the upper nozzles and air from the lower nozzles at a propane:ammonia:oxygen molar ratio of 1:0.87:2.85 for a contact time of 2.82 sec·g/cm$^3$. The oxygen concentration in the generated gas at the reactor outlet was 2.61%. This reaction was continued for 1 week.
(Ammoxidation Reaction Stopping)

The supply of propane, ammonia, and air was concurrently stopped, and 128,700 L of nitrogen (an amount 225 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 2 hours 30 minutes, and the time required until the temperature decreased to 360° C. was 3 hours 30 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Working Example 5

Vapor-Phase Contact Ammoxidation Reaction

A vapor-phase contact ammoxidation reaction was carried out using the same catalyst as in Working Example 1. The reactor type, the reaction temperature, and the reaction pressure were the same as in Working Example 1. The supply of the raw material gases was carried out by supplying propane and ammonia from the upper nozzles and air from the lower nozzles at a propane:ammonia:oxygen molar ratio of 1:0.85:2.85 for a contact time of 2.85 sec·g/cm$^3$. The oxygen concentration in the generated gas at the reactor outlet was 2.65%. This reaction was continued for 1 week.
(Ammoxidation Reaction Stopping)

The supply of propane, ammonia, and air was concurrently stopped, and 157,300 L of nitrogen (an amount 275 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 1 hour 30 minutes, and the time required until the temperature decreased to 360° C. was 2 hours. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Working Example 6

Vapor-Phase Contact Ammoxidation Reaction

A vapor-phase contact ammoxidation reaction was carried out using the same catalyst as in Working Example 1. The reactor type, the reaction temperature, and the reaction pressure were the same as in Working Example 1. The supply of the raw material gases was carried out by supplying propane and ammonia from the upper nozzles and air from the lower nozzles at a propane:ammonia:oxygen molar ratio of 1:0.98:2.5 for a contact time of 3.00 sec·g/cm$^3$. The oxygen concentration in the generated gas at the reactor outlet was 1.35%. This reaction was continued for 1 week.
(Ammoxidation Reaction Stopping)

The supply of propane, ammonia, and air was concurrently stopped, and 8,580 L of nitrogen (an amount 15 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 8 hours 6 minutes, and the time required until the temperature decreased to 360° C. was 8 hours 48 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Working Example 7

Vapor-Phase Contact Ammoxidation Reaction

A vapor-phase contact ammoxidation reaction was carried out using the same catalyst as in Working Example 1. The reactor type, the reaction temperature, and the reaction pressure were the same as in Working Example 1. The supply of the raw material gases was carried out by supplying propane and ammonia from the upper nozzles and air from the lower nozzles at a propane:ammonia:oxygen molar ratio of 1:0.90:2.85 for a contact time of 2.95 sec·g/cm$^3$. The oxygen concentration in the generated gas at the reactor outlet was 2.35%. This reaction was continued for 1 week.
(Ammoxidation Reaction Stopping)

The supply of propane, ammonia, and air was concurrently stopped, and 14,300 L of nitrogen (an amount 25 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 7 hours 12 minutes, and the time required until the temperature decreased to 360° C. was 8 hours. The supply of nitrogen was continued until the catalyst layer temperature reached 380° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 1

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped. The time required from when the supply of the raw material gases was stopped until the catalyst layer temperature decreased to 380° C. was 22 hours, and the time required until the temperature decreased to 360° C. was 25 hours. After the catalyst temperature reached 360° C., 14,300 L of air (an amount 25 times the catalyst volume) was supplied per hour until the catalyst layer temperature reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 2

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 1,716 L of nitrogen (an amount 3 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 16 hours, and the time required until the temperature decreased to 360° C. was 18 hours. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 3

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 4,004 L of nitrogen (an amount 7 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 12 hours 18 minutes, and the time required until the temperature decreased to 360° C. was 14 hours 30 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 4

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 188,760 L of nitrogen (an amount 330 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 1 hour 12 minutes, and the time required until the temperature decreased to 360° C. was 1 hour 30 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 5

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 211,640 L of nitrogen (an amount 370 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 54 minutes, and the time required until the temperature decreased to 360° C. was 1 hour 15 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 6

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 240,240 L of nitrogen (an amount 420 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 36 minutes, and the time required until the temperature decreased to 360° C. was 48 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the catalyst remaining in the reactor had remarkably decreased, so that the reaction could not be restarted unless more catalyst was newly added. The acrylonitrile yield, the rate of change in the reduction rate of the catalyst before and after the reaction was stopped, and the activity are shown in Table 1.

Comparative Example 7

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 28,600 L of nitrogen (an amount 50 times the catalyst volume) was supplied per hour from the lower nozzles placed pointing vertically upwards from the bottom face of the catalyst loaded portion of the reactor. The supply of nitrogen was continued for 4 hours until the catalyst layer temperature reached 400° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 8

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 5,720 L of nitrogen (an amount 10 times the catalyst volume) was supplied per hour from the lower nozzles placed vertically upwards from the bottom face of the catalyst loaded portion of the reactor. The time required from when the supply of the raw material gases was stopped until the catalyst layer temperature decreased to 380° C. was 10 hours 30 minutes, and the time required until the temperature decreased to 360° C. was 12 hours. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 9

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 45,760 L of air (an amount 80 times the catalyst volume) was supplied per hour from the lower nozzles placed vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 30 minutes. The supply of air was continued until the catalyst layer temperature reached 360° C. (inert gas cutoff temperature). Subsequently, the supply of air was continued until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 10

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 45,760 L of nitrogen containing 5% by volume of oxygen (an amount 80 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 30 minutes. The supply of the oxygen-containing nitrogen was continued until the catalyst layer temperature reached 360° C. (inert gas cutoff temperature). Subsequently, the same amount of air was supplied until the temperature of the catalyst layer reached 100° C. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Comparative Example 11

Ammoxidation Reaction Stopping

A vapor-phase contact ammoxidation reaction was carried out in the same manner as in Working Example 1 using the same catalyst as in Working Example 1. The supply of propane, ammonia, and air was concurrently stopped, and 45,760 L of a gas prepared by mixing air and ammonia in a 4:1 ratio (an amount 80 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 30 minutes. The supply of the mixed gas of air and ammonia was continued until the catalyst layer temperature reached 360° C. (inert gas cutoff temperature). Subsequently, the supply of the mixed gas was continued until the temperature of the catalyst layer reached 100° C. and the same amount of air was supplied. After the stopping, the ammoxidation reaction was restarted under the same conditions as in Working Example 1 using the catalyst remaining in the reactor. The acrylonitrile yield, the rate of change in the reduction rate of the catalyst before and after the reaction was stopped, and the activity are shown in Table 1.

Reference Example 1

Catalyst Preparation

A catalyst was prepared by supporting a metal oxide having the below-described composition on a 50 wt % silica carrier based on the method described in Japanese Patent Publication No. S57-26592. The main calcining was carried out for 2 hours at 790° C. $Mo_{0.8}Sb_{20}Fe_{10}W_{0.2}Te_{1.7}Na_{0.15}Cu_{2.5}$ (Vapor-Phase Contact Ammoxidation Reaction)

573 kg of the obtained catalyst was loaded into a SUS fluidized bed reactor having an inner diameter of 600 mm. The bulk specific gravity of the catalyst was 1 kg/L, and the catalyst volume was 573 L. Upper nozzles for supplying a gas containing propylene and ammonia were placed pointing vertically downwards at a position 30 cm above the bottom face of the catalyst loaded portion of the reactor. The placement positions were the center of the reactor, and at the apexes of a square having 340 mm sides with the center of the reactor as its center (total of 5 locations). Lower nozzles for supplying a gas containing oxygen were placed pointing vertically upwards at the bottom face of the catalyst loaded portion of the reactor. The placement positions of the lower nozzles were set so as to overlap in the vertical direction the upper nozzles for supplying a gas containing propylene and ammonia (5 locations). For heat removal in the reactor, four stationary-used cooling coils and two cooling coils for fine adjustments to the temperature were placed in the catalyst dense layer.

At a reactor temperature of 440° C. and reaction pressure of 50 kPa, propylene and ammonia were supplied from the upper nozzles and air was supplied from the lower nozzles at a propylene:ammonia:oxygen molar ratio of 1:1.1:1.89 for a contact time of 3.5 sec·g/cm$^3$. The oxygen concentration in the generated gas at the reactor outlet was 0.2%. This reaction was continued for 1 week.

(Ammoxidation Reaction Stopping)

The supply of propylene, ammonia, and air was concurrently stopped, and 1,719 L of nitrogen (an amount 3 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 17 hours, and the time required until the temperature decreased to 360° C. was 14 hours. The supply of nitrogen was continued until the catalyst layer temperature reached 360° C. (inert gas cutoff temperature). Subsequently, the same amount of air as the nitrogen was supplied until the temperature of the catalyst layer reached 100° C. After stopping of the ammoxidation reaction, the ammoxidation reaction was restarted under the same conditions as before the reaction was stopped using the catalyst remaining in the reactor. The acrylonitrile yield and the activity are shown in Table 1.

Reference Example 2

Vapor-Phase Contact Ammoxidation Reaction

A vapor-phase contact ammoxidation reaction was carried out using the same catalyst as in Reference Example 1. The reactor type, the reaction temperature, the reaction pressure, and the amount of gas supplied were the same as in Reference Example 1.

(Ammoxidation Reaction Stopping)

The supply of propylene, ammonia, and air was concurrently stopped, and 14,325 L of nitrogen (an amount 25 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 7 hours, and the time required until the temperature decreased to 360° C. was 8 hours. The supply of nitrogen was continued for 9 hours until the catalyst layer temperature reached 340° C. (inert gas cutoff temperature). Subsequently, the same amount of air as the nitrogen was supplied until the temperature of the catalyst layer reached 100° C. After the stopping, the ammoxidation reaction was restarted under the same conditions as in Reference Example 1 using the catalyst remaining in the reactor. The acrylonitrile yield and the activity are shown in Table 1.

Reference Example 3

Vapor-Phase Contact Ammoxidation Reaction

A vapor-phase contact ammoxidation reaction was carried out using the same catalyst as in Reference Example 1. The reactor type, the reaction temperature, the reaction pressure, and the amount of gas supplied were the same as in Reference Example 1.
(Ammoxidation Reaction Stopping)
The supply of propylene, ammonia, and air was concurrently stopped, and 45,840 L of nitrogen (an amount 80 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 18 minutes. The supply of nitrogen was continued for 5 hours 42 minutes until the catalyst layer temperature reached 375° C. (inert gas cutoff temperature). Subsequently, the same amount of air as the nitrogen was supplied until the temperature of the catalyst layer reached 100° C. After the stopping, the ammoxidation reaction was restarted under the same conditions as in Reference Example 1 using the catalyst remaining in the reactor. The acrylonitrile yield and the activity are shown in Table 1.

Reference Example 4

Vapor-Phase Contact Ammoxidation Reaction

A vapor-phase contact ammoxidation reaction was carried out using the same catalyst as in Reference Example 1. The reactor type, the reaction temperature, the reaction pressure, and the amount of gas supplied were the same as in Reference Example 1.
(Ammoxidation Reaction Stopping)
The supply of propylene, ammonia, and air was concurrently stopped, and 85,950 L of nitrogen (an amount 150 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 4 hours, and the time required until the temperature decreased to 360° C. was 5 hours 12 minutes. The supply of nitrogen was continued until the catalyst layer temperature reached 360° C. (inert gas cutoff temperature). Subsequently, the same amount of air as the nitrogen was supplied until the temperature of the catalyst layer reached 100° C. After the stopping, the ammoxidation reaction was restarted under the same conditions as in Reference Example 1 using the catalyst remaining in the reactor. The acrylonitrile yield and the activity are shown in Table 1.

Reference Example 5

Vapor-Phase Contact Ammoxidation Reaction

A vapor-phase contact ammoxidation reaction was carried out using the same catalyst as in Reference Example 1. The reactor type, the reaction temperature, the reaction pressure, and the amount of gas supplied were the same as in Reference Example 1.
(Ammoxidation Reaction Stopping)
The supply of propylene, ammonia, and air was concurrently stopped, and 45,840 L of air (an amount 80 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 30 minutes. The supply of air was continued until the catalyst layer temperature reached 100° C. After the stopping, the ammoxidation reaction was restarted under the same conditions as in Reference Example 1 using the catalyst remaining in the reactor. The acrylonitrile yield and the activity are shown in Table 1.

Reference Example 6

Vapor-Phase Contact Ammoxidation Reaction

A vapor-phase contact ammoxidation reaction was carried out using the same catalyst as in Reference Example 1. The reactor type, the reaction temperature, the reaction pressure, and the amount of gas supplied were the same as in Reference Example 1.
(Ammoxidation Reaction Stopping)
The supply of propylene, ammonia, and air was concurrently stopped, and 45,840 L of nitrogen containing 5% by volume of oxygen (an amount 80 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 30 minutes. The supply of nitrogen containing 5% by volume of oxygen was continued until the catalyst layer temperature reached 360° C. (inert gas cutoff temperature). Subsequently, air was continued to be supplied until the temperature of the catalyst layer reached 100° C. After the stopping, the ammoxidation reaction was restarted under the same conditions as in Reference Example 1 using the catalyst remaining in the reactor. The acrylonitrile yield and the activity are shown in Table 1.

Reference Example 7

Vapor-Phase Contact Ammoxidation Reaction

A vapor-phase contact ammoxidation reaction was carried out using the same catalyst as in Reference Example 1. The reactor type, the reaction temperature, the reaction pressure, and the amount of gas supplied were the same as in Reference Example 1.
(Ammoxidation Reaction Stopping)
The supply of propylene, ammonia, and air was concurrently stopped, and 45,840 L of a gas prepared by mixing air and ammonia in a 4:1 ratio (an amount 80 times the catalyst volume) was supplied per hour from the lower nozzles placed pointing vertically upwards from the bottom face of the catalyst loaded portion of the reactor. The time required from when the supply of the raw material gases was stopped until the catalyst layer temperature decreased to 380° C. was 5 hours 30 minutes, and the time required until the temperature decreased to 360° C. was 6 hours 30 minutes. The supply of the mixed gas of air and ammonia was continued until the catalyst layer temperature reached 360° C. (inert gas cutoff temperature). Subsequently, air was continued to be supplied until the temperature of the catalyst layer reached 100° C. After the stopping, the ammoxidation reaction was restarted under the same conditions as in Reference Example 1 using the catalyst remaining in the reactor. The acrylonitrile yield and the activity are shown in Table 1.

TABLE 1

| Working Example Comparative Example | Raw Material Gas | Inert Gas Type | Amount of Gas/Catalyst Volume (per hour) | Inert Gas Cutoff Temperature (° C.) | Inert Gas Flow Time (h) | Time Taken until Reaching 360° C. (h) |
|---|---|---|---|---|---|---|
| Working Example 1 | Propane | Inert gas ($N_2$) | 25 | 340 | 9 | 8 |
| Working Example 2 | Propane | Inert gas ($N_2$) | 80 | 375 | 5.7 | 6.5 |
| Working Example 3 | Propane | Inert gas ($N_2$) | 150 | 360 | 5.2 | 5.2 |
| Working Example 4 | Propane | Inert gas ($N_2$) | 225 | 360 | 3.5 | 3.5 |
| Working Example 5 | Propane | Inert gas ($N_2$) | 275 | 360 | 2 | 2 |
| Working Example 6 | Propane | Inert gas ($N_2$) | 15 | 360 | 8.8 | 8.8 |
| Working Example 7 | Propane | Inert gas ($N_2$) | 25 | 380 | 7.2 | 8 |
| Comparative Example 1 | Propane | Inert gas ($N_2$) | 0 | 360 | 0 | 25 |
| Comparative Example 2 | Propane | Inert gas ($N_2$) | 3 | 360 | 16 | 16 |
| Comparative Example 3 | Propane | Inert gas ($N_2$) | 7 | 360 | 14.5 | 14.5 |
| Comparative Example 4 | Propane | Inert gas ($N_2$) | 330 | 360 | 1.5 | 1.5 |
| Comparative Example 5 | Propane | Inert gas ($N_2$) | 370 | 360 | 1.25 | 1.25 |
| Comparative Example 6 | Propane | Inert gas ($N_2$) | 420 | 360 | 0.8 | 0.8 |
| Comparative Example 7 | Propane | Inert gas ($N_2$) | 50 | 400 | 4 | — |
| Comparative Example 8 | Propane | Inert gas ($N_2$) | 10 | 360 | 12 | 12 |
| Comparative Example 9 | Propane | Air | 80 | 360 | 0 | 6.5 |
| Comparative Example 10 | Propane | Oxygen-containing $N_2$ gas (oxygen 5 vol. %) | 80 | 360 | 0 | 6.5 |
| Comparative Example 11 | Propane | Mixed gas (air:$NH_3$ = 4:1) | 80 | 360 | 0 | 6.5 |
| Reference Example 1 | Propylene | Inert gas ($N_2$) | 3 | 360 | 14 | 14 |
| Reference Example 2 | Propylene | Inert gas ($N_2$) | 25 | 340 | 9 | 8 |
| Reference Example 3 | Propylene | Inert gas ($N_2$) | 80 | 375 | 5.7 | 6.3 |
| Reference Example 4 | Propylene | Inert gas ($N_2$) | 150 | 360 | 5.2 | 5.2 |
| Reference Example 5 | Propylene | Air | 80 | 360 | 0 | 6.5 |
| Reference Example 6 | Propylene | Oxygen-containing $N_2$ gas 5 vol. % | 80 | 360 | 0 | 6.5 |
| Reference Example 7 | Propylene | Mixed gas (air:$NH_3$ = 4:1) | 80 | 360 | 0 | 6.5 |

| Working Example Comparative Example | Time Taken until Reaching 380° C. (h) | Rate of Change in Reduction Rate (%) | Amount of Catalyst Scattered (%) | Activity Before Stoppage | Activity After Re-SU | Acrylonitrile Yield (%) Before Stoppage | Acrylonitrile Yield (%) After Re-SU |
|---|---|---|---|---|---|---|---|
| Working Example 1 | 7 | 2.19 | 4.0 | 3.00 | 2.90 | 55.4 | 55.2 |
| Working Example 2 | 5.5 | 1.51 | 5.0 | 3.11 | 3.03 | 55.2 | 55.1 |
| Working Example 3 | 4 | 0.82 | 5.9 | 3.15 | 3.08 | 55.3 | 55.2 |
| Working Example 4 | 2.5 | 0.57 | 9.4 | 3.10 | 3.05 | 55.4 | 55.4 |
| Working Example 5 | 1.5 | 0.41 | 12.2 | 3.04 | 3.01 | 55.5 | 55.5 |
| Working Example 6 | 8.1 | 3.01 | 3.6 | 3.13 | 3.01 | 55.6 | 55.3 |
| Working Example 7 | 7.2 | 4.11 | 3.6 | 3.02 | 2.80 | 55.4 | 55 |
| Comparative Example 1 | 22 | 8.51 | 1.0 | 3.02 | 2.64 | 55.3 | 51.3 |
| Comparative Example 2 | 18 | 6.42 | 2.1 | 3.10 | 2.78 | 55.4 | 52.3 |
| Comparative Example 3 | 12.3 | 5.01 | 3.0 | 3.05 | 2.82 | 55.3 | 53.4 |
| Comparative Example 4 | 1.2 | 0.29 | 20.1 | 3.10 | 3.08 | 55.4 | 55.4 |
| Comparative Example 5 | 0.9 | 0.15 | 31.2 | 2.98 | 2.99 | 55.3 | 55.4 |
| Comparative Example 6 | 0.6 | 0.08 | 40.3 | 2.95 | — | 55.4 | — |
| Comparative Example 7 | — | 6.01 | 3.8 | 3.10 | 3.31 | 55.4 | 52.2 |
| Comparative Example 8 | 10.5 | 5.05 | 5.5 | 3.02 | 3.04 | 55.6 | 53.2 |
| Comparative Example 9 | 5.5 | 8.77 | 5.3 | 3.10 | 3.35 | 55.4 | 51.0 |
| Comparative Example 10 | 5.5 | 6.45 | 4.8 | 3.01 | 3.21 | 55.3 | 52.4 |
| Comparative Example 11 | 5.5 | 6.11 | 5.1 | 3.00 | 2.88 | 55.5 | 53.4 |
| Reference Example 1 | 17 | — | 2.2 | 4.40 | 4.40 | 81.1 | 80.9 |
| Reference Example 2 | 7 | — | 4.2 | 4.50 | 4.52 | 81.2 | 81 |
| Reference Example 3 | 5.5 | — | 4.8 | 4.58 | 4.60 | 80.9 | 80.9 |
| Reference Example 4 | 4 | — | 6.4 | 4.55 | 4.55 | 81 | 81.1 |
| Reference Example 5 | 5.5 | — | 5.1 | 4.55 | 4.55 | 81.1 | 81.1 |
| Reference Example 6 | 5.5 | — | 5.2 | 4.58 | 4.60 | 80.9 | 81 |
| Reference Example 7 | 5.5 | — | 5.5 | 4.55 | 4.54 | 80.9 | 80.9 |

In Comparative Examples 4 and 5, the amount of inert gas was too large, so a large amount of catalyst was scattered. In Comparative Example 6, the catalyst was scattered because the amount of inert gas supplied was too large, so the reaction could not be carried out again. Further, in Comparative Examples 1, 2, 3, 7, 8, 9, 10, and 11, it was found from the rate of change in the reduction rate and the AN yield that catalytic activity deteriorated. In contrast, the Working Examples showed that the ammoxidation reaction can be stopped safely and rapidly while suppressing deterioration in the catalytic activity.

The present application is based on a Japanese patent application filed with the Japan Patent Office on Oct. 1, 2012 (Japanese Patent Application No. 2012-219398), the contents of which are hereby incorporated in their entirety.

INDUSTRIAL APPLICABILITY

The method for stopping an ammoxidation reaction according to the present invention can be preferably employed in the safe and rapid production of acrylonitrile.

The invention claimed is:

1. A method for stopping an ammoxidation reaction comprising:

a supply stopping step of stopping a supply of propane, an oxygen-containing gas, and ammonia to a reactor where an ammoxidation reaction of propane is being carried out using a catalyst comprising Mo, V, Nb, and Sb; and a reaction stopping step of supplying an inert gas to the reactor in an amount 10 to 300 times the catalyst volume per hour until a catalyst temperature reaches 380° C. or less, wherein after the supply stopping step, a time required until the catalyst temperature decreases to 360° C. or less is within 10 hours.

2. A method for producing an acrylonitrile comprising:

a supply stopping step of stopping a supply of propane, an oxygen-containing gas, and ammonia to a reactor where an ammoxidation reaction of propane is being carried out using a catalyst comprising Mo, V, Nb, and Sb; and a reaction stopping step of supplying an inert gas to the reactor in an amount 10 to 300 times the catalyst volume per hour until a catalyst temperature reaches 380° C. or less, wherein after the supply stopping step, a time required until the catalyst temperature decreases to 360° C. or less is within 10 hours.

* * * * *